(12) United States Patent
Ritzberger et al.

(10) Patent No.: US 11,325,858 B2
(45) Date of Patent: May 10, 2022

(54) LITHIUM SILICATE-LOW QUARTZ GLASS CERAMIC

(71) Applicant: Ivoclar Vivadent AG, Schaan (LI)

(72) Inventors: Christian Ritzberger, Grabs (CH); Markus Rampf, Lachen (CH); Wolfram Höland, Schaan (LI); Marc Dittmer, Feldkirch (AT); Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 50 days.

(21) Appl. No.: 16/656,639

(22) Filed: Oct. 18, 2019

(65) Prior Publication Data

US 2020/0079685 A1 Mar. 12, 2020

Related U.S. Application Data

(63) Continuation of application No. 15/753,350, filed as application No. PCT/EP2016/069807 on Aug. 22, 2016, now Pat. No. 10,501,366.

(30) Foreign Application Priority Data

Aug. 25, 2015 (EP) .................................. 15182307
Oct. 20, 2015 (EP) .................................. 15190547

(51) Int. Cl.
*C03C 10/00* (2006.01)
*C03C 3/087* (2006.01)
*C03C 3/097* (2006.01)
*A61K 6/833* (2020.01)
*C03C 4/00* (2006.01)

(52) U.S. Cl.
CPC .......... *C03C 10/0027* (2013.01); *A61K 6/833* (2020.01); *C03C 3/087* (2013.01); *C03C 3/097* (2013.01); *C03C 4/0021* (2013.01); *C03C 2203/10* (2013.01)

(58) Field of Classification Search
CPC .. C03C 10/00; C03C 10/0009; C03C 10/0027
See application file for complete search history.

(56) References Cited

U.S. PATENT DOCUMENTS

| | | | | |
|---|---|---|---|---|
| 5,507,981 A ‡ | 4/1996 | Petticrew | ............... | A61C 13/20 264/16 |
| 5,626,935 A * | 5/1997 | Goto | .................. | C03C 10/0009 428/64.1 |
| 5,702,514 A ‡ | 12/1997 | Petticrew | ............... | A61C 13/20 106/35 |
| 5,866,489 A ‡ | 2/1999 | Yamaguchi | ......... | C03C 10/0027 501/4 |
| 7,316,740 B2 ‡ | 1/2008 | Schweiger | .......... | C03C 10/0036 106/35 |
| 9,232,989 B2 ‡ | 1/2016 | Ritzberger | .............. | C03B 32/02 |
| 9,371,249 B2 ‡ | 6/2016 | Ritzberger | ........... | A61K 6/0205 |
| 9,688,567 B2 ‡ | 6/2017 | Rampf | ..................... | C03C 3/112 |
| 2007/0082294 A1 * | 4/2007 | Goto | .................... | C03C 10/0045 430/270.12 |
| 2008/0248316 A1 ‡ | 10/2008 | Goto | ....................... | C03B 27/02 428/42 |
| 2009/0162608 A1 * | 6/2009 | Yagi | .................... | C03C 10/0009 428/141 |
| 2015/0104655 A1 * | 4/2015 | Kim | ....................... | C03B 19/02 428/432 |
| 2015/0274581 A1 * | 10/2015 | Beall | ....................... | C03C 3/097 501/4 |
| 2018/0009701 A1 ‡ | 1/2018 | Rampf | ................ | C03C 10/0009 |

FOREIGN PATENT DOCUMENTS

| | | | |
|---|---|---|---|
| CA | 2252660 A1 ‡ | 5/1999 | |
| CA | 2252660 A1 | 5/1999 | |
| CN | 104108883 A | 10/2014 | |
| EP | 827941 A1 ‡ | 3/1998 | |
| EP | 827941 A1 | 3/1998 | |
| EP | 1688398 A1 ‡ | 8/2006 | |
| EP | 1688398 A1 | 8/2006 | |

OTHER PUBLICATIONS

International Preliminary Report on Patentability of PCT/EP2016/069807, dated Feb. 27, 2018, 8 pages.‡
Dittmer, Dr. Marc, "Glasses and glass-ceramics in the system of MgO—Al2O3—SiO2 with ZrO2 as nucleating agent," Dissertation of Dr. Marc Dittmer, 2011.‡
Dittmer, Dr. Marc, "Glasses and glass-ceramics in the system of MgO—Al2O3—SiO2 with ZrO2 as nucleating agent," Dissertation of Dr. Marc Dittmer, 2011.

* cited by examiner
‡ imported from a related application

*Primary Examiner* — Noah S Wiese
(74) *Attorney, Agent, or Firm* — Ann M. Knab; Thad McMurray

(57) ABSTRACT

Lithium silicate-low quartz glass ceramics are described which are characterized by a combination of very good mechanical and optical properties and can therefore be used in particular as restoration material in dentistry.

23 Claims, No Drawings

LITHIUM SILICATE-LOW QUARTZ GLASS CERAMIC

CROSS-REFERENCE TO RELATED APPLICATIONS

This application is a continuation application and claims priority to U.S. application Ser. No. 15/753,350, filed Feb. 19, 2018, which is the National Stage application of International patent application PCT/EP2016/069807 filed on Aug. 22, 2016, which claims priority to European patent application No. 15182307.7 filed on Aug. 25, 2015, and European patent application No. 15190547.8 filed on Oct. 20, 2015, all the disclosures of which are incorporated herein by reference in their entirety.

FIELD OF THE INVENTION

The invention relates to lithium silicate-low quartz-glass ceramic which is suitable in particular for use in dentistry, preferably for the preparation of dental restorations, as well as to precursors for the preparation of this glass ceramic.

BACKGROUND

Lithium silicate glass ceramics are characterized as a rule by very good mechanical properties, which is why they have been used for some time in the dental field, and there primarily for the preparation of dental crowns and small dental bridges.

U.S. Pat. Nos. 5,507,981 and 5,702,514 describe lithium disilicate glass ceramics which are processed to form dental restorations by pressing in the viscous state. However, the use of a deformable crucible is essential, which makes the processing very expensive.

EP 827 941 and EP 916 625 disclose lithium disilicate glass ceramics which can be given the shape of the desired dental restoration by pressing or machining.

EP 1 505 041 and EP 1 688 398 describe processes for the preparation of dental restorations from lithium disilicate glass ceramics. As an intermediate product a glass ceramic with lithium metasilicate as main crystal phase, which can be very easily machined e.g. by means of CAD/CAM processes, is produced first. This intermediate product is then subjected to a further heat treatment in order to form the desired high-strength lithium disilicate glass ceramic. The heat treatments used during the process are to be chosen such that the formation of undesired crystal phases, such as for example cristobalite, is prevented.

WO 2013/053864 discloses lithium silicate glass ceramics which contain divalent metal oxide and can be processed to form dental restorations by hot pressing as well as by machining.

Glass ceramics are known from WO 2013/164256 which have lithium disilicate as main crystal phase and apatite as a further crystal phase. The glass ceramics are characterized by high chemical stability and can be shaped to form the desired dental restorations by machining or hot pressing.

US 2015/0104655 describes glass ceramics which, depending on the composition and the temperature treatment chosen for the crystallization, can contain lithium disilicate, lithium metasilicate, lithium phosphate, cristobalite, tridymite, quartz or spodumene as crystal phases. The glass ceramics are intended in particular to veneer zirconium oxide ceramics.

However, the machining of the conventional lithium disilicate glass ceramics is possible only with difficulty because of their high strength and it therefore as a rule involves a high wear of the tools used. The likewise possible machining of corresponding lithium metasilicate glass ceramics as precursors is much easier. However, this requires yet a further heat treatment to produce the restoration from high-strength lithium disilicate glass ceramic after the shaping by machining.

There is therefore a need for lithium silicate glass ceramics which are easily machinable and do not require a further heat treatment after this processing in order to give the produced dental restoration the desired mechanical properties. The lithium silicate glass ceramics are to have not only very good mechanical properties, but likewise also very good optical properties, in order that they also fulfil the high aesthetic demands which are made on a restorative dental material.

SUMMARY

This object is achieved by the lithium silicate-low quartz glass ceramic according to claims 1 to 14 and 17. Also a subject of the invention are the starting glass according to claims 15, 16 and 17, the process according to claims 18, 19 and 22 as well as the use according to claims 20 and 21.

DETAILED DESCRIPTION

The lithium silicate-low quartz glass ceramic according to the invention is characterized in that it comprises lithium silicate as main crystal phase and low quartz as further crystal phase.

It has surprisingly been shown that the glass ceramic according to the invention unites a combination of very desirable mechanical and optical properties, such as are necessary precisely for a restorative dental material. The glass ceramic has a high strength and nevertheless it can be given the shape of a dental restoration easily by machining. There is no need for a subsequent heat treatment to achieve a satisfactory strength. It was furthermore not to be expected that very good optical properties can nevertheless be achieved by the provision of low quartz as further crystal phase in addition to lithium silicate as main crystal phase. This is because many additional crystal phases have a negative effect on the optical properties of lithium silicate glass ceramics. For example they can decrease the translucence and they can likewise impair the ability of the glass ceramic to be dyed, which can lead to substantial difficulties in the imitation of the colour of the natural tooth material to be replaced.

The lithium silicate-low quartz glass ceramic according to the invention in particular comprises 59.0 to 79.0, preferably 64.0 to 78.0 and particularly preferably 64.0 to 76.0 wt.-% $SiO_2$.

In another embodiment, the lithium silicate-low quartz glass ceramic according to the invention in particular comprises 68.0 to 79.0, preferably 69.0 to 78.0 and particularly preferably 70.0 to 76.0 wt.-% $SiO_2$.

It is further preferred that the lithium silicate-low quartz glass ceramic according to the invention comprises 8.0 to 15.0, particularly preferably 9.0 to 14.0 and quite particularly preferably 10.0 to 13.5 wt.-% $Li_2O$. It is assumed that $Li_2O$ lowers the viscosity of the glass matrix and thus promotes the crystallization of the desired phases.

In a further preferred embodiment, the glass ceramic comprises 0 to 9.0, preferably 2.0 to 6.0 and particularly preferably 3.0 to 5.0 wt.-% $P_2O_5$. It is assumed that the $P_2O_5$ acts as nucleating agent.

It is also preferred that the glass ceramic comprises 1.0 to 8.0 and in particular 2.0 to 7.0 wt.-% oxide of monovalent elements $Me^{I}_2O$ selected from the group of $K_2O$, $Na_2O$, $Rb_2O$, $Cs_2O$ and mixtures thereof.

The glass ceramic particularly preferably comprises at least one and in particular all of the following oxides of monovalent elements $Me^{I}_2O$ in the amounts specified:

| Component | wt.-% |
| --- | --- |
| $K_2O$ | 0 to 5.0 |
| $Na_2O$ | 0 to 2.0 |
| $Rb_2O$ | 0 to 8.0 |
| $Cs_2O$ | 0 to 7.0. |

In a particularly preferred embodiment, the glass ceramic according to the invention comprises 0 to 5.0, preferably 1.0 to 4.0 and particularly preferably 2.0 to 3.5 wt.-% $K_2O$.

Furthermore, it is preferred that the glass ceramic comprises 1.0 to 9.0, preferably 2.0 to 8.0 and particularly preferably 3.0 to 7.0 wt.-% oxide of divalent elements $Me^{II}O$ selected from the group of CaO, MgO, SrO, ZnO and mixtures thereof.

In a further preferred embodiment, the glass ceramic comprises less than 2.0 wt.-% BaO. The glass ceramic is in particular substantially free from BaO.

The glass ceramic preferably comprises at least one and in particular all of the following oxides of divalent elements $Me^{II}O$ in the amounts specified:

| Component | wt.-% |
| --- | --- |
| CaO | 0 to 3.0 |
| MgO | 0 to 6.0 |
| SrO | 0 to 4.0 |
| ZnO | 0 to 9.0 |

In a particularly preferred embodiment, the glass ceramic according to the invention comprises 1.0 to 6.0, in particular 1.5 to 6.0, preferably 2.0 to 5.5, particularly preferably 3.1 to 5.5 and quite particularly preferably 3.4 to 5.0 wt.-% MgO.

A glass ceramic is further preferred which comprises 0 to 8.0, preferably 1.0 to 7.0 and particularly preferably 2.0 to 6.5 wt.-% oxide of trivalent elements $Me^{III}_2O_3$ selected from the group of $Al_2O_3$, $B_2O_3$, $Y_2O_3$, $La_2O_3$, $Ga_2O_3$, $In_2O_3$ and mixtures thereof.

The glass ceramic particularly preferably comprises at least one and in particular all of the following oxides of trivalent elements $Me^{III}_2O_3$ in the amounts specified:

| Component | wt.-% |
| --- | --- |
| $Al_2O_3$ | 1.0 to 6.0 |
| $B_2O_3$ | 0 to 4.0 |
| $Y_2O_3$ | 0 to 5.0 |
| $La_2O_3$ | 0 to 5.0 |
| $Ga_2O_3$ | 0 to 3.0 |
| $In_2O_3$ | 0 to 5.0 |

In a particularly preferred embodiment, the glass ceramic according to the invention comprises 1.0 to 6.0 and preferably 2.0 to 5.0 wt.-% $Al_2O_3$.

Furthermore, a glass ceramic is preferred which comprises 0 to 10.0 and particularly preferably 0 to 8.0 wt.-% oxide of tetravalent elements $Me^{IV}O_2$ selected from the group of $ZrO_2$, $TiO_2$, $SnO_2$, $CeO_2$, $GeO_2$ and mixtures thereof.

The glass ceramic particularly preferably comprises at least one and in particular all of the following oxides of tetravalent elements $Me^{IV}O_2$ in the amounts specified:

| Component | wt.-% |
| --- | --- |
| $ZrO_2$ | 0 to 3.0 |
| $TiO_2$ | 0 to 4.0 |
| $SnO_2$ | 0 to 3.0 |
| $GeO_2$ | 0 to 9.0, in particular 0 to 8.0 |
| $CeO_2$ | 0 to 4.0. |

In a further embodiment, the glass ceramic comprises 0 to 8.0, preferably 0 to 6.0 wt.-% oxide of pentavalent elements $Me^{V}_2O_5$ selected from the group of $V_2O_5$, $Ta_2O_5$, $Nb_2O_5$ and mixtures thereof.

The glass ceramic particularly preferably comprises at least one and in particular all of the following oxides of pentavalent elements $Me^{V}_2O_5$ in the amounts specified:

| Component | wt.-% |
| --- | --- |
| $V_2O_5$ | 0 to 2.0 |
| $Ta_2O_5$ | 0 to 5.0 |
| $Nb_2O_5$ | 0 to 5.0 |

In a further embodiment, the glass ceramic comprises 0 to 5.0, preferably 0 to 4.0 wt.-% oxide of hexavalent elements $Me^{VI}O_3$ selected from the group of $WO_3$, $MoO_3$ and mixtures thereof.

The glass ceramic particularly preferably comprises at least one and in particular all of the following oxides $Me^{VI}O_3$ in the amounts specified:

| Component | wt.-% |
| --- | --- |
| $WO_3$ | 0 to 3.0 |
| $MoO_3$ | 0 to 3.0 |

In a further embodiment, the glass ceramic according to the invention comprises 0 to 1.0 and in particular 0 to 0.5 wt.-% fluorine.

A glass ceramic is particularly preferred which comprises at least one and preferably all of the following components in the amounts specified:

| Component | wt.-% |
| --- | --- |
| $SiO_2$ | 59.0 to 79.0 or 68.0 to 79.0 |
| $Li_2O$ | 8.0 to 15.0 |
| $P_2O_5$ | 0 to 9.0 |
| $Me^{I}_2O$ | 1.0 to 8.0 |
| $Me^{II}O$ | 1.0 to 9.0 |
| $Me^{III}_2O_3$ | 0 to 8.0 |
| $Me^{IV}O_2$ | 0 to 10.0 |
| $Me^{V}_2O_5$ | 0 to 8.0 |
| $Me^{VI}O_3$ | 0 to 5.0 |
| fluorine | 0 to 1.0, | wherein $Me^{I}_2O$, $Me^{II}O$, $Me^{III}_2O_3$, $Me^{IV}O_2$, $Me^{V}_2O_5$ and $Me^{VI}O_3$ have the above-specified meaning.

In a further particularly preferred embodiment, the glass ceramic comprises at least one and preferably all of the following components in the amounts specified:

| Component | wt.-% |
| --- | --- |
| SiO$_2$ | 59.0 to 79.0 or 68.0 to 79.0 |
| Li$_2$O | 8.0 to 15.0 |
| P$_2$O$_5$ | 0 to 9.0 |
| K$_2$O | 0 to 5.0 |
| Na$_2$O | 0 to 2.0 |
| Rb$_2$O | 0 to 8.0 |
| Cs$_2$O | 0 to 7.0 |
| CaO | 0 to 3.0 |
| MgO | 0 to 6.0 |
| SrO | 0 to 4.0 |
| ZnO | 0 to 9.0 |
| Al$_2$O$_3$ | 1.0 to 6.0 |
| B$_2$O$_3$ | 0 to 4.0 |
| Y$_2$O$_3$ | 0 to 5.0 |
| La$_2$O$_3$ | 0 to 5.0 |
| Ga$_2$O$_3$ | 0 to 3.0 |
| In$_2$O$_3$ | 0 to 5.0 |
| ZrO$_2$ | 0 to 3.0 |
| TiO$_2$ | 0 to 4.0 |
| SnO$_2$ | 0 to 3.0 |
| GeO$_2$ | 0 to 9.0, in particular 0 to 8.0 |
| CeO$_2$ | 0 to 4.0 |
| V$_2$O$_5$ | 0 to 2.0 |
| Ta$_2$O$_5$ | 0 to 5.0 |
| Nb$_2$O$_5$ | 0 to 5.0 |
| WO$_3$ | 0 to 3.0 |
| MoO$_3$ | 0 to 3.0 |
| fluorine | 0 to 1.0. |

Some of the above-named components can serve as colorants and/or fluorescent agents. The glass ceramic according to the invention can also comprise still further colorants and/or fluorescent agents. These can e.g. be selected from Bi$_2$O$_3$ or Bi$_2$O$_5$ and in particular from further inorganic pigments and/or oxides of d-block and f-block elements, such as the oxides of Mn, Fe, Co, Pr, Nd, Tb, Er, Dy, Eu and Yb. With the aid of these colorants and fluorescent agents a simple dying of the glass ceramic is possible in order to imitate the desired optical properties in particular of natural tooth material. It is surprising that this is possible without problems despite the low quartz present as further crystal phase.

In a preferred embodiment of the glass ceramic the molar ratio of SiO$_2$ to Li$_2$O lies in the range of from 2.2 to 4.1, preferably 2.2 to 3.8 and particularly preferably 2.2 to 3.5. It is surprising that the preparation of the glass ceramic according to the invention with lithium silicate as main crystal phase and low quartz as further crystal phase is achieved within these broad ranges.

The term "main crystal phase" refers to the crystal phase which has the highest proportion by mass of all the crystal phases present in the glass ceramic. The masses of the crystal phases are determined in particular using the Rietveld method. A suitable process for the quantitative analysis of the crystal phases by means of the Rietveld method is described e.g. in M. Dittmer's doctoral thesis "Glasses and glass ceramics in the MgO—Al$_2$O$_3$—SiO$_2$ system with ZrO$_2$ as nucleating agent", University of Jena 2011.

It is preferred that the glass ceramic according to the invention comprises lithium disilicate or lithium metasilicate as main crystal phase. In a particularly preferred embodiment, the glass ceramic according to the invention comprises lithium disilicate as main crystal phase, as this glass ceramic has a particularly advantageous combination of desirable properties.

In the case of a glass ceramic according to the invention with lithium metasilicate as main crystal phase it is preferred that the glass ceramic also comprises lithium disilicate as further crystal phase in addition to low quartz.

It is preferred that the glass ceramic according to the invention has at least 20 wt.-%, preferably 25 to 55 wt.-% and particularly preferably 30 to 55 wt.-% lithium disilicate crystals.

It is further preferred that the glass ceramic according to the invention has 0.2 to 28 wt.-% and particularly preferably 0.5 to 25 wt.-% low quartz crystals.

The glass ceramic according to the invention can comprise, in addition to lithium silicate and low quartz, still further crystal phases, such as apatite, caesium aluminosilicate and in particular lithium phosphate. However, the amount of cristobalite should be as small as possible, and in particular should be less than 1.0 wt.-%. It is particularly preferred that the glass ceramic according to the invention is substantially free from cristobalite.

The type and in particular the amount of the crystal phases formed can be controlled by the composition of the starting glass as well as the heat treatment which is used to prepare the glass ceramic from the starting glass. The examples illustrate this with reference to the variation in the composition of the starting glass and the heat treatment used.

The glass ceramic has a high biaxial breaking strength of preferably at least 200 MPa and particularly preferably 250 to 460 MPa. The biaxial breaking strength was determined according to ISO 6872 (2008) (piston-on-three-ball test).

It is particularly surprising that, despite this high breaking strength, the glass ceramic according to the invention can be machined easily and quickly by means of computer-assisted milling and grinding apparatuses in order to give the glass ceramic e.g. the shape of a dental restoration.

The glass ceramic according to the invention has a coefficient of thermal expansion CTE (measured in the range of 100 to 500° C.) of preferably 9.5 to 14.0·10$^{-6}$K$^{-1}$. The CTE is determined according to ISO 6872 (2008). The coefficient of thermal expansion is adjusted to a desired value in particular by the type and amount of the crystal phases present in the glass ceramic as well as the chemical composition of the glass ceramic.

The translucence of the glass ceramic was determined in the form of the contrast value (CR value) according to British Standard BS 5612, and this contrast value was preferably 40 to 92.

The particular combination of properties present in the case of the glass ceramic according to the invention even allows it to be used as dental material and in particular as material for the preparation of dental restorations.

The invention likewise relates to various precursors with a corresponding composition from which the lithium silicate-low quartz glass ceramic according to the invention can be prepared by heat treatment. These precursors are a starting glass with a corresponding composition and a starting glass with nuclei with a corresponding composition. The term "corresponding composition" means that these precursors comprise the same components in the same amounts as the glass ceramic, wherein the components with the exception of fluorine are calculated as oxides, as is usual for glasses and glass ceramics.

The invention therefore also relates to a starting glass which comprises the components of the lithium disilicate-low quartz glass ceramic according to the invention.

The starting glass according to the invention therefore comprises in particular suitable amounts of SiO$_2$ and Li$_2$O which are required to form the glass ceramic according to the invention with lithium silicate as main crystal phase and low quartz as further crystal phase. Further, the starting glass can also comprise still other components, such as are specified above for the lithium silicate-low quartz glass ceramic according to the invention. All those embodiments which are specified as preferred for the components of the lithium silicate-low quartz glass ceramic according to the invention are also preferred for the components of the starting glass.

The invention also relates to such a starting glass which comprises nuclei for the crystallization of lithium metasilicate, lithium disilicate and/or low quartz.

The further precursor starting glass with nuclei can be produced first by heat treatment of the starting glass. The lithium silicate-low quartz glass ceramic according to the invention can then be produced by heat treatment of this further precursor. It is preferred to form the lithium silicate-low quartz glass ceramic according to the invention by heat treatment of the starting glass with nuclei.

It is preferred to subject the starting glass to a heat treatment at a temperature of 400 to 600° C., in particular 450 to 550° C., for a period of preferably 5 to 120 min, in particular 10 to 60 min, in order to produce the starting glass with nuclei for the crystallization of lithium metasilicate, lithium disilicate and/or low quartz.

It is further preferred to subject the starting glass with nuclei to a heat treatment at a temperature of 700 to 900° C. for a period of in particular 1 to 120 min, preferably 5 to 120 min, particularly preferably 10 to 60 min, in order to prepare the lithium silicate-low quartz glass ceramic. To prepare the lithium silicate-low quartz glass ceramic the heat treatment of the starting glass with nuclei particularly preferably takes place at 700 to 880° C., in particular 750 to 850° C., for a period of preferably 5 to 120 min, particularly preferably 10 to 60 min.

The invention also relates to a process for the preparation of the lithium silicate-low quartz glass ceramic according to the invention, in which the starting glass or the starting glass with nuclei is subjected to at least one heat treatment at a temperature of 700 to 900° C. for a period of in particular 1 to 120 min, preferably 5 to 120 min and particularly preferably 10 to 60 min.

The starting glass and the starting glass with nuclei can be subjected to the at least one heat treatment e.g. in the form of a solid glass blank, a powder compact or a powder.

The at least one heat treatment carried out in the process according to the invention can also take place during a hot pressing or sintering-on of the starting glass according to the invention or of the starting glass with nuclei according to the invention.

In a preferred embodiment the process according to the invention comprises
(a) the heat treatment of the starting glass at a temperature of 400 to 600° C. in order to form the starting glass with nuclei, and
(b) the heat treatment of the starting glass with nuclei at a temperature of 700 to 900° C. in order to form the lithium silicate-low quartz glass ceramic.

The duration of the heat treatments carried out in (a) and (b) is in particular 5 to 120 min and preferably 10 to 60 min.

To prepare the starting glass, the procedure is in particular that a mixture of suitable starting materials, such as carbonates, oxides, phosphates and fluorides, is melted at temperatures of in particular 1300 to 1600° C. for 2 to 10 h. To achieve a particularly high homogeneity, the obtained glass melt is poured into water in order to form a granular glass material, and the obtained granulate is then melted again.

The melt can then be poured into moulds in order to produce blanks of the starting glass, so-called solid glass blanks or monolithic blanks.

It is also possible to put the melt into water again in order to prepare a granulate. This granulate can be pressed, after grinding and optionally addition of further components, such as colorants and fluorescent agents, to form a blank, a so-called powder compact.

Finally, the starting glass can also be processed to form a powder after granulation.

The starting glass, e.g. in the form of a solid glass blank, a powder compact or in the form of a powder, is then subjected to at least one heat treatment. It is preferred that a first heat treatment is carried out first in order to prepare a starting glass according to the invention with nuclei which are suitable for forming lithium metasilicate, lithium disilicate and/or low quartz crystals. The glass with nuclei is then usually subjected to at least one further temperature treatment at a higher temperature in order to effect crystallization of lithium silicate, in particular of lithium disilicate, and low quartz.

The glass ceramics according to the invention and the glasses according to the invention are present in particular in the form of powders, granulates or blanks of any shape and size, e.g. monolithic blanks, such as platelets, cuboids or cylinders, or powder compacts, in unsintered, partially sintered or densely sintered form. They can easily be further processed in these forms. They can, however, also be present in the form of dental restorations, such as inlays, onlays, crowns, veneers, facets or abutments.

Dental restorations, such as bridges, inlays, onlays, crowns, veneers, facets or abutments, can be prepared from the glass ceramics according to the invention and the glasses according to the invention. The invention therefore also relates to their use for the preparation of dental restorations. It is preferred that the glass ceramic or the glass is given the shape of the desired dental restoration by pressing or machining.

The pressing is usually carried out under increased pressure and at increased temperature. It is preferred that the pressing is carried out at a temperature of 700 to 1200° C. It is further preferred to carry out the pressing at a pressure of 2 to 10 bar. During pressing, the desired change in shape is achieved by viscous flow of the material used. The starting glass according to the invention and in particular the starting glass with nuclei according to the invention, and the lithium silicate-low quartz glass ceramic according to the invention, can be used for the pressing. The glasses and glass ceramics according to the invention can be used in particular in the form of blanks in any shape and size, e.g. solid blanks or powder compacts, e.g. in unsintered, partially sintered or densely sintered form.

The machining is usually carried out by material removal processes and in particular by milling and/or grinding. It is particularly preferred that the machining is carried out during a CAD/CAM process. The starting glass according to the invention, the starting glass with nuclei according to the invention and the lithium silicate-low quartz glass ceramic according to the invention can be used for the machining. The glasses and glass ceramics according to the invention can be used in particular in the form of blanks, e.g. solid blanks or powder compacts, e.g. in unsintered, partially sintered or densely sintered form. The lithium silicate-low quartz glass ceramic according to the invention is preferably used for the machining.

After the preparation of the dental restoration shaped as desired, e.g. by pressing or machining, it can still be heat-treated in order to reduce the porosity, e.g. of a porous powder compact used.

However, the glass ceramics according to the invention and the glasses according to the invention are also suitable as coating material for e.g. ceramics and glass ceramics. The invention is therefore also directed towards the use of the glasses according to the invention or the glass ceramics according to the invention for coating in particular ceramics and glass ceramics.

The invention also relates to a process for coating ceramics, metals, metal alloys and glass ceramics, in which glass ceramic according to the invention or glass according to the invention is applied to the ceramic or glass ceramic and exposed to increased temperature.

This can be carried out in particular by sintering-on or joining of an overstructure prepared by means of CAD/CAM using a suitable glass solder or adhesive, and preferably by pressing-on. In the case of sintering-on, the glass ceramic or the glass is applied to the material to be coated, such as ceramic or glass ceramic, in the usual way, e.g. as a powder, and then sintered at increased temperature. In the case of the preferred pressing-on, glass ceramic according to the invention or glass according to the invention is pressed on, e.g. in the form of powder compacts or monolithic blanks, at an increased temperature of e.g. 700 to 1200° C., and with the application of pressure, e.g. 2 to 10 bar. For this, in particular the processes described in EP 231 773 and the press furnace disclosed there can be used. A suitable furnace is e.g. the Programat EP 5000 from Ivoclar Vivadent AG, Liechtenstein.

It is preferred that, after conclusion of the coating process, the glass ceramic according to the invention is present with lithium silicate, in particular lithium disilicate, as main crystal phase and low quartz as further crystal phase, as such a glass ceramic has particularly good properties.

Because of the above-described properties of the glass ceramics according to the invention and the glasses according to the invention, these are suitable in particular for use in dentistry. A subject of the invention is therefore also the use of the glass ceramics according to the invention or the glasses according to the invention as dental material and in particular for the preparation of dental restorations or as coating material for dental restorations, such as crowns, bridges and abutments.

The invention is explained in more detail below with reference to non-limiting examples.

EXAMPLES

Examples 1 to 34—Composition and Crystal Phases

A total of 34 glasses and glass ceramics according to the invention with the composition specified in Table I were prepared by melting corresponding starting glasses as well as subsequent heat treatments for controlled nucleation and crystallization.

The heat treatments used for controlled nucleation and controlled crystallization are also specified in Table I. The following meanings apply $T_g$ Glass transition temperature, determined by means of DSC $T_S$ and $t_S$ Temperature and time used for melting the starting glass $T_{Kb}$ and $t_{Kb}$ Temperature and time used for nucleation of the starting glass $T_C$ and $t_C$ Temperature and time used for the crystallization $T_{press}$ and $t_{press}$ Temperature and time used for crystallization by hot pressing CR value Contrast value of the glass ceramic according to British Standard BS 5612 determined using:
  Apparatus: CM-3700d spectrometer (Konica-Minolta)
  Measurement parameters:
  Measurement area: 7 mm×5 mm
  Type of measurement: reflectance/reflection
  Measurement range: 400 nm-700 nm
  Sample size:
  Diameter: 15-20 mm
  Thickness: 2 mm+/−0.025 mm
  Plane parallelism: +/−0.05 mm
  Surface roughness: about 18 μm.

CTE Coefficient of thermal expansion of the glass ceramic according to ISO 6872 (2008), measured in the range of 100 to 500° C.

$\sigma_{Biax}$ Biaxial breaking strength, measured according to dental standard ISO 6872 (2008)

The amounts of the crystal phases were determined by means of the Rietveld method. For this, powders of the respective glass ceramic were used which were mixed with $Al_2O_3$ (product name: Taimicron TM-DAR, from: Taimei Chemicals, Co. Ltd., Japan) as internal standard in a ratio of 50 wt.-% glass ceramic to 50 wt.-% $Al_2O_3$. This mixture was slurried with acetone in order to achieve as good a thorough mixing as possible. The mixture was then dried at about 80° C. Then a diffractogram in the range 10 to 100° 2θ was acquired by means of a D8 Advance diffractometer from Bruker using $Cu_{K\alpha}$ radiation and a step size of 0.014° 2θ. This diffractogram was then evaluated with the TOPAS software from Bruker, and the phase proportions were determined. For all diffractograms a lower limit of about 30 nm for the $Li_3PO_4$ crystallite size was used.

To produce the glasses and glass ceramics according to the invention the starting glasses in a range of 100 to 200 g were first melted from customary raw materials at 1500° C. or 1400° C. for a period of 1 to 3 hours, wherein the melting was very easily possible without formation of bubbles or streaks. By pouring the starting glasses into water, glass frits were prepared which were then melted a second time at 1500° C. or 1400° C. for 1 hour for homogenization.

A first heat treatment of the starting glasses at a temperature of 460 to 550° C. led to the formation of glasses with nuclei. As a result of a further heat treatment at 760 to 880° C., these nuclei-containing glasses crystallized to form glass ceramics with lithium silicate as main crystal phase and low quartz as further crystal phase, as was established by X-ray diffraction tests. Thus, lithium silicate-low quartz glass ceramics according to the invention were obtained.

A) Solid Glass Blocks

In Examples 1-26, 28 and 31-34 the glass ceramics were prepared from solid glass blocks. For this, the obtained glass granulates were melted again at the temperature $T_S$ for a period $t_S$. The obtained melts of the starting glass were then poured into a graphite mould in order to produce solid glass blocks. These glass monoliths were then stress relieved at the temperature $T_{Kb}$ for a period $t_{Kb}$, whereby nucleation was able to take place. The nuclei-containing starting glasses were then heated to a temperature $T_C$ for a period $t_C$. Glass ceramics according to the invention with lithium disilicate as main crystal phase and low quartz as additional phase were thereby formed, as could be established by X-ray diffraction tests at room temperature.

It is assumed that in this process variant a volume crystallization of lithium disilicate and low quartz has taken place.

B) Powder Compacts

In Example 27 the glass ceramic was prepared from powder compacts. For this, the obtained glass granulate was ground in a zirconium oxide mill to a particle size of <90 μm. About 4 g of this powder was then pressed to form cylindrical blanks and sintered in a sinter furnace (Programat® from Ivoclar Vivadent AG) at a temperature $T_C$ and a holding time of $t_C$ to form dense glass ceramic bodies. A glass ceramic according to the invention with lithium metasilicate as main crystal phase as well as lithium disilicate and low quartz as additional phases was formed by the sintering, as could be established by X-ray diffraction tests at room temperature.

C) Preparation of a Dental Restoration from Blocks According to A

The glass ceramic blocks produced according to Examples 1-26, 28 and 31-34 were machined in a CAD/CAM unit to form desired dental restorations, such as crowns. For this, the crystallized blocks were provided with a suitable holder, and then given the desired shape in an inLab MC XL grinding unit from Sirona Dental GmbH, Germany. For the processing of the blanks according to the invention it was possible to use the same grinding parameters as for commercial e.max CAD blocks, Ivoclar Vivadent, Liechtenstein.

D) Hot Pressing of the Glass Ceramic

In Example 19, for which $T_{press}$ and $t_{press}$ are specified, the glass ceramic was prepared from solid glass blocks by hot pressing.

For this, the obtained glass granulate was melted again at the temperature $T_S$ for a period $t_S$. The obtained melt of the starting glass was then poured into a pre-heated steel mould in order to produce rods. These monolithic glass rods were then stress relieved at a temperature $T_{Kb}$ for a period $t_{Kb}$, whereby nucleation was able to take place. The rods were then sawn to form small cylinders with a mass of about 4 to 6 g. These small cylinders were then crystallized at a temperature $T_C$ for a period of $t_C$. The nucleated and crystallized cylinders were then pressed to form a shaped body in a hot-pressing furnace at the temperature $T_{press}$ and for a holding time of $t_{press}$. A glass ceramic according to the invention with lithium disilicate as main crystal phase and low quartz as further crystal phase had formed after the hot-pressing, as could be established by X-ray diffraction tests of the formed shaped body at room temperature.

E) Sintering of a Nucleated Glass

In Example 29 the starting glass was melted at 1500° C. for 2 h and then quenched in water. The obtained glass granulate was then nucleated at a temperature $T_{Kb}$ and for a time $t_{Kb}$. The nucleated starting glass was comminuted to form a powder with an average particle size of 20 μm. A test piece was prepared from this nucleated glass powder to determine the thermal expansion and to determine the optical properties, and crystallized and densely sintered at a temperature of $T_C$ and for a time $t_C$. After the dense sintering a glass ceramic according to the invention with lithium disilicate as main crystal phase and low quartz as further additional phase had formed, as could be established by X-ray diffraction tests of the formed shaped body at room temperature.

TABLE 1

| Composition | Example No. | | | | |
|---|---|---|---|---|---|
| | 1 wt.-% | 2 wt.-% | 3 wt.-% | 4 wt.-% | 5 wt.-% |
| $SiO_2$ | 74.3 | 73.3 | 72.0 | 72.0 | 74.9 |
| $Li_2O$ | 11.2 | 12.6 | 13.3 | 12.3 | 10.7 |
| $K_2O$ | 3.4 | 3.2 | 3.5 | 3.4 | 3.4 |
| $Rb_2O$ | — | — | — | — | — |
| MgO | 4.4 | 1.4 | 4.5 | 4.4 | 4.4 |
| CaO | — | 1.9 | — | — | — |
| SrO | — | — | — | — | — |
| $Al_2O_3$ | 2.8 | 3.5 | 2.8 | 2.8 | 2.8 |
| $Ga_2O_3$ | — | — | — | — | — |
| $Er_2O_3$ | — | — | — | 0.1 | — |
| $CeO_2$ | — | — | — | 0.8 | — |
| $V_2O_5$ | — | — | — | 0.1 | — |
| $P_2O_5$ | 3.9 | 4.1 | 3.9 | 3.9 | 3.8 |
| $F^-$ | — | — | — | — | — |
| $Tb_4O_7$ | — | — | — | 0.3 | — |
| $T_g/°$ C. | 471 | 465 | 469 | 463 | 471 |
| $T_s/°$ C., $t_s$/min | 1500, 120 | 1520, 120 | 1500, 120 | 1500, 120 | 1500, 120 |
| $T_{Kb}/°$ C., $t_{Kb}$/min | 500, 30 | 480, 10 | 500, 30 | 500, 30 | 500, 30 |
| $T_C/°$ C., $t_C$/min | 800, 30 | 800, 15 | 800, 30 | 810, 20 | 800, 30 |
| Main crystal phase (wt.-%) | $Li_2Si_2O_5$ (40.9) | $Li_2Si_2O_5$ | $Li_2Si_2O_5$ (51.3) | $Li_2Si_2O_5$ (43.4) | $Li_2Si_2O_5$ (36.2) |
| Further crystal phases (wt.-%) | Low quartz (17.5), $Li_3PO_4$ (6.3) | Low quartz, $Li_3PO_4$ | Low quartz (0.2), $Li_3PO_4$ (6.8) | Low quartz (4.4), $Li_3PO_4$ (6.0), | Low quartz (20.7), $Li_3PO_4$ (5.4) |
| $\sigma_{Biax}$/MPa | 464 | | | 376 | |
| CR value | 71.83 | | | 71.45 | 71.21 |
| L* | 94.15 | | | 89.46 | 93.90 |

TABLE 1-continued

| | | | | | |
|---|---|---|---|---|---|
| a* | −0.45 | | | 0.48 | −0.40 |
| b* | 3.44 | | | 13.22 | 3.92 |
| CTE/$10^{-6}K^{-1}$ (100-500° C.) | | | | | |

| | Example No. | | | | |
|---|---|---|---|---|---|
| Composition | 6 wt.-% | 7 wt.-% | 8 wt.-% | 9 wt.-% | 10 wt.-% |
| $SiO_2$ | 72.3 | 72.6 | 70.1 | 73.0 | 75.6 |
| $Li_2O$ | 12.0 | 11.7 | 11.3 | 11.4 | 10.2 |
| $K_2O$ | 3.4 | 3.4 | — | 3.4 | 3.4 |
| $Rb_2O$ | — | — | 6.5 | — | — |
| MgO | 4.4 | 4.4 | 4.2 | 4.4 | 4.3 |
| CaO | — | — | — | — | — |
| SrO | — | — | — | — | — |
| $Al_2O_3$ | 2.8 | 2.8 | 2.2 | 2.8 | 2.7 |
| $Ga_2O_3$ | — | — | — | — | — |
| $Er_2O_3$ | 0.1 | 0.1 | 0.1 | 0.1 | — |
| $CeO_2$ | 0.8 | 0.8 | 0.7 | 0.6 | — |
| $V_2O_5$ | 0.1 | 0.1 | 0.1 | 0.1 | — |
| $P_2O_5$ | 3.9 | 3.8 | 4.5 | 3.8 | 3.8 |
| $F^-$ | — | — | — | — | — |
| $Tb_4O_7$ | 0.3 | 0.3 | 0.3 | 0.4 | — |
| $T_g$/° C. | 469 | 473 | 472 | 470 | 480 |
| $T_s$/° C., $t_s$/min | 1500, 120 | 1500, 120 | 1500, 120 | 1500, 120 | 1500, 120 |
| $T_{Kb}$/° C., $t_{Kb}$/min | 480, 60 | 520, 10 | 480, 120 | 470, 10 | 500, 30 |
| $T_c$/° C., $t_c$/min | 800, 30 | 820, 10 | 800, 30 | 780, 30 | 800, 30 |
| Main crystal phase (wt.-%) | $Li_2Si_2O_5$ (42.7) | $Li_2Si_2O_5$ (39.0) | $Li_2Si_2O_5$ (30.0) | $Li_2Si_2O_5$ (38.4) | $Li_2Si_2O_5$ (32.7) |
| Further crystal phases (wt.-%) | Low quartz (10.2), $Li_3PO_4$ (6.0) | Low quartz (12.1), $Li_3PO_4$ (6.0) | Low quartz (7.1), $Li_3PO_4$ (7.1) | Low quartz (14.8), $Li_3PO_4$ (5.6) | Low quartz (24.2), $Li_3PO_4$ (6.3) |
| $\sigma_{Biax}$/MPa | 371 | 395 | 456 | 326 | 347 |
| CR value | 69.27 | 68.94 | 77.14 | 68.63 | 71.28 |
| L* | 89.78 | 89.68 | 90.06 | 90.29 | 94.07 |
| a* | 0.34 | 0.18 | −0.13 | 0.85 | −0.46 |
| b* | 13.65 | 13.9 | 9.07 | 11.17 | 3.46 |
| CTE/$10^{-6}K^{-1}$ (100-500° C.) | 10.8 | 11.3 | | 11.5 | |

| | Example No. | | | | |
|---|---|---|---|---|---|
| Composition | 11 wt.-% | 12 wt.-% | 13 wt.-% | 14 wt.-% | 15 wt.-% |
| $SiO_2$ | 72.9 | 72.2 | 70.2 | 72.4 | 70.4 |
| $Li_2O$ | 11.3 | 11.6 | 12.5 | 10.9 | 12.1 |
| $K_2O$ | 2.1 | 3.4 | 3.3 | 3.4 | 3.1 |
| $Rb_2O$ | — | — | — | — | — |
| MgO | 1.8 | 4.4 | 1.6 | 4.3 | 3.4 |
| CaO | 1.8 | — | 2.3 | — | — |
| SrO | 3.3 | — | — | — | — |
| $Al_2O_3$ | 2.7 | 4.6 | 4.0 | 3.9 | 3.6 |
| $Ga_2O_3$ | — | — | — | — | 2.5 |
| $Er_2O_3$ | — | — | 0.2 | 0.2 | 0.1 |
| $CeO_2$ | — | — | 1.2 | 0.6 | 0.9 |
| $V_2O_5$ | — | — | 0.1 | 0.1 | 0.1 |
| $P_2O_5$ | 3.8 | 3.8 | 4.3 | 3.8 | 3.5 |
| $F^-$ | 0.3 | — | — | — | — |
| $Tb_4O_7$ | — | — | 0.3 | 0.4 | 0.3 |
| $T_g$/° C. | 453 | 477 | 464 | 472 | 462 |
| $T_s$/° C., $t_s$/min | 1500, 120 | 1500, 120 | 1500, 120 | 1500, 120 | 1500, 120 |
| $T_{Kb}$/° C., $t_{Kb}$/min | 460, 90 | 500, 30 | 500, 10 | 480, 40 | 540, 10 |
| $T_c$/° C., $t_c$/min | 800, 40 | 800, 30 | 800, 60 | 770, 60 | 790, 30 |
| Main crystal phase (wt.-%) | $Li_2Si_2O_5$ (45.0) | $Li_2Si_2O_5$ (38.7) | $Li_2Si_2O_5$ (38.1) | $Li_2Si_2O_5$ (34.4) | $Li_2Si_2O_5$ (39.0) |
| Further crystal phases (wt.-%) | Low quartz (19.3), $Li_3PO_4$ (2.8), $Ca_2Sr_3(PO_4)_3F$ (5.5) | Low quartz (13.4), $Li_3PO_4$ (5.4) | Low quartz (9.4), $Li_3PO_4$ (6.3) | Low quartz (17.4), $Li_3PO_4$ (5.2) | Low quartz (9.9), $Li_3PO_4$ (5.4) |
| $\sigma_{Biax}$/MPa | 397 | | 350 | 377 | 285 |
| CR value | 70.06 | | 64.56 | 69.01 | 70.84 |
| L* | 89.22 | | 85.82 | 90.67 | 86.98 |
| a* | 0.50 | | 2.6 | 1.95 | 1.80 |
| b* | 5.87 | | 19.74 | 8.96 | 19.10 |

TABLE 1-continued

| | | | | | |
|---|---|---|---|---|---|
| CTE/10⁻⁶K⁻¹ (100-500° C.) | | | | 10.6 | 10.8 |

| | Example No. | | | | |
|---|---|---|---|---|---|
| Composition | 16 wt.-% | 17 wt.-% | 18 wt.-% | 19 wt.-% | 20 wt.-% |
| $SiO_2$ | 69.2 | 71.5 | 71.0 | 74.7 | 70.0 |
| $Li_2O$ | 11.5 | 10.5 | 10.0 | 9.8 | 10.5 |
| $K_2O$ | 3.2 | 3.3 | 3.3 | 3.3 | 3.2 |
| $Cs_2O$ | — | — | — | — | — |
| $Rb_2O$ | — | — | — | — | — |
| MgO | 3.1 | 3.5 | 3.8 | 4.3 | 3.8 |
| CaO | — | — | — | — | — |
| SrO | — | — | — | — | — |
| ZnO | — | — | — | — | — |
| $Al_2O_3$ | 3.1 | 2.8 | 3.0 | 2.9 | 3.8 |
| $Ga_2O_3$ | — | — | — | — | — |
| $La_2O_3$ | — | — | 3.4 | — | — |
| $Y_2O_3$ | — | 2.9 | — | — | — |
| $In_2O_3$ | 4.7 | — | — | — | — |
| $Er_2O_3$ | 0.2 | 0.1 | 0.1 | 0.1 | 0.2 |
| $ZrO_2$ | — | — | — | — | — |
| $SnO_2$ | — | — | — | — | — |
| $CeO_2$ | 1.0 | 0.6 | 1.2 | 0.8 | 0.5 |
| $MnO_2$ | — | — | — | — | — |
| $V_2O_5$ | 0.1 | 0.1 | 0.1 | 0.1 | 0.1 |
| $Ta_2O_5$ | — | — | — | — | 3.8 |
| $P_2O_5$ | 3.5 | 4.3 | 3.7 | 3.6 | 3.7 |
| $F^-$ | — | — | — | — | — |
| $Tb_4O_7$ | 0.4 | 0.4 | 0.4 | 0.4 | 0.4 |
| $T_g$/° C. | 483 | 477 | 478 | 467 | 482 |
| $T_s$/° C., $t_s$/min | 1500, 120 | 1500, 120 | 1500, 120 | 1500, 120 | 1500, 120 |
| $T_{Kb}$/° C., $t_{Kb}$/min | 550, 30 | 480, 10 | 500, 40 | 470, 60 | 500, 20 |
| $T_c$/° C., $t_c$/min | 770, 20 | 760, 10 | 760, 20 | 750, 30 | 760, 30 |
| $T_{press}$/° C., $t_{press}$/° C. | | | | 870, 25 | |
| Main crystal phase (wt.-%) | $Li_2Si_2O_5$ (32.4) | $Li_2Si_2O_5$ (27.0) | $Li_2Si_2O_5$ (27.3) | $Li_2Si_2O_5$ (28.8) | $Li_2Si_2O_5$ (29.1) |
| Further crystal phases (wt.-%) | Low quartz (9.8), $Li_3PO_4$ (4.9), | Low quartz (19.9), $Li_3PO_4$ (6.0) | Low quartz (18.6), $Li_3PO_4$ (5.1) | Low quartz (24.3), $Li_3PO_4$ (3.8) | Low quartz (14.8), $Li_3PO_4$ (4.4) |
| $\sigma_{Biax}$/MPa | 299 | 290 | 320 | | 367 |
| CR value | 57.60 | 56.69 | 46.84 | 64.29 | 63.10 |
| L* | 85.77 | 90.49 | 84.38 | 90.6 | 89.91 |
| a* | 0.16 | −0.50 | 0.05 | 0.38 | 1.70 |
| b* | 19.18 | 9.68 | 26.72 | 12.76 | 9.43 |
| CTE/10⁻⁶K⁻¹ (100-500° C.) | | | | 12.8 | |

| | Example No. | | | | |
|---|---|---|---|---|---|
| Composition | 21 wt.-% | 22 wt.-% | 23 wt.-% | 24 wt.-% | 25 wt.-% |
| $SiO_2$ | 72.9 | 68.8 | 69.5 | 73.2 | 73.7 |
| $Li_2O$ | 12.5 | 11.4 | 11.5 | 11.7 | 11.5 |
| $K_2O$ | 3.5 | 3.3 | 3.3 | 0.8 | 3.3 |
| $Cs_2O$ | — | — | — | 1.3 | — |
| $Rb_2O$ | — | — | — | 1.3 | — |
| MgO | 4.4 | 3.2 | 1.1 | 2.9 | — |
| CaO | — | — | 1.5 | — | — |
| SrO | — | — | 2.4 | — | 3.6 |
| ZnO | — | — | 1.8 | — | — |
| $Al_2O_3$ | 2.8 | 3.2 | 2.7 | 2.7 | 2.5 |
| $Ga_2O_3$ | — | — | — | — | — |
| $La_2O_3$ | — | — | — | — | — |
| $Y_2O_3$ | — | — | — | — | — |
| $In_2O_3$ | — | — | — | — | — |
| $Er_2O_3$ | — | 0.2 | 0.2 | 0.1 | 0.1 |
| $ZrO_2$ | — | 2.1 | — | — | — |
| $SnO_2$ | — | 2.6 | — | — | — |
| $CeO_2$ | — | 1.1 | 1.8 | 1.5 | 1.5 |
| $MnO_2$ | — | — | — | 0.1 | — |
| $V_2O_5$ | — | 0.1 | 0.2 | 0.2 | 0.1 |
| $Ta_2O_5$ | — | — | — | — | — |
| $P_2O_5$ | 3.9 | 3.6 | 3.7 | 3.8 | 3.3 |
| $F^-$ | — | — | — | — | — |
| $Tb_4O_7$ | — | 0.4 | 0.3 | 0.4 | 0.4 |

TABLE 1-continued

| | | | | | |
|---|---|---|---|---|---|
| $T_g/°C.$ | 473 | 483 | 461 | 467 | 472 |
| $T_s/°C., t_s/min$ | 1500, 120 | 1500, 120 | 1500, 120 | 1500, 120 | 1500, 120 |
| $T_{Kb}/°C., t_{Kb}/min$ | 500, 30 | 490, 30 | 480, 30 | 500, 20 | 500, 70 |
| $T_c/°C., t_c/min$ | 800, 30 | 770, 40 | 800, 10 | 820, 30 | 830, 40 |
| $T_{press}/°C., t_{press}/°C.$ | | | | | |
| Main crystal phase (wt.-%) | $Li_2Si_2O_5$ (48.0) | $Li_2Si_2O_5$ | $Li_2Si_2O_5$ | $Li_2Si_2O_5$ | $Li_2Si_2O_5$ (37.3) |
| Further crystal phases (wt.-%) | Low quartz (6.5), $Li_3PO_4$ (6.6), | Low quartz, $Li_3PO_4$ | Low quartz, $Li_3PO_4$ | Low quartz, $Li_3PO_4$ | Low quartz (14.7), $Li_3PO_4$ (2.1) |
| $\sigma_{Biax}/MPa$ | | | 487 | | |
| CR value | 74.98 | | 53.15 | | |
| L* | 94.16 | | 79.74 | | |
| a* | −0.62 | | 3.58 | | |
| b* | 3.40 | | 34.15 | | |
| $CTE/10^{-6}K^{-1}$ (100-500° C.) | | | | | |

| | Example No. | | | |
|---|---|---|---|---|
| Composition | 26 wt.-% | 27 wt.-% | 28 wt.-% | 29 wt.-% |
| $SiO_2$ | 73.0 | 74.8 | 68.9 | 75.8 |
| $Li_2O$ | 11.7 | 13.3 | 12.2 | 10.5 |
| $K_2O$ | 3.4 | 3.6 | 3.3 | 3.4 |
| $Cs_2O$ | — | — | — | — |
| $Rb_2O$ | — | — | — | — |
| MgO | 4.4 | 1.7 | 1.4 | 3.6 |
| CaO | — | 2.4 | 2.1 | — |
| SrO | — | — | — | — |
| ZnO | — | — | — | — |
| $Al_2O_3$ | 3.7 | 4.2 | 3.9 | 2.9 |
| $Ga_2O_3$ | — | — | — | — |
| $La_2O_3$ | — | — | — | — |
| $Y_2O_3$ | — | — | — | — |
| $In_2O_3$ | — | — | — | — |
| $Er_2O_3$ | — | — | — | — |
| $ZrO_2$ | — | — | — | — |
| $SnO_2$ | — | — | — | — |
| $CeO_2$ | — | — | — | — |
| $MnO_2$ | — | — | — | — |
| $V_2O_5$ | — | — | — | — |
| $Ta_2O_5$ | — | — | — | — |
| $P_2O_5$ | 3.8 | — | 8.2 | 3.8 |
| $F^-$ | — | — | — | — |
| $Tb_4O_7$ | — | — | — | — |
| $T_g/°C.$ | | 457 | 471 | 469; |
| $T_s/°C., t_s/min$ | 1500, 120 | 1500, 180 | 1500, 150 | 1500, 120 |
| $T_{Kb}/°C., t_{Kb}/min$ | 500, 30 | — | 490, 10 | 500, 30 |
| $T_c/°C., t_c/min$ | 800, 30 | 780, 10 | 800, 30 | 880, 1 |
| $T_{press}/°C., t_{press}/°C.$ | | | | |
| Main crystal phase (wt.-%) | $Li_2Si_2O_5$ (45.0) | $Li_2SiO_3$, | $Li_2Si_2O_5$, | $Li_2Si_2O_5$, |
| Further crystal phases (wt.-%) | Low quartz (12.8), $Li_3PO_4$ (6.0) | Low quartz, $Li_2Si_2O_5$, $Li_3PO_4$ | Low quartz, $Li_3PO_4$ | Low quartz, $Li_3PO_4$ |
| $\sigma_{Biax}/MPa$ | | | 320 | |
| CR value | | | 67.66 | 76.6 |
| L* | | | 91.17 | 94 |
| a* | | | 0.08 | −0.21 |
| b* | | | 4.69 | 2.55 |
| $CTE/10^{-6}K^{-1}$ (100-500° C.) | | | | 12.3 |

| | Example No. | | | | |
|---|---|---|---|---|---|
| Composition | 30 wt.-% | 31 wt.-% | 32 wt.-% | 33 wt.-% | 34 wt.-% |
| $SiO_2$ | 64.4 | 67.1 | 69.8 | 71.6 | 59.7 |
| $Li_2O$ | 14.6 | 13.3 | 11.9 | 11.1 | 12.9 |
| $Na_2O$ | — | — | 1.6 | 1.9 | — |
| $K_2O$ | 3.3 | 3.3 | — | — | 3.2 |
| $Cs_2O$ | — | — | 5.0 | 3.7 | — |
| $Rb_2O$ | — | — | — | — | — |
| MgO | — | — | 3.9 | 3.2 | 0.2 |
| CaO | — | — | — | — | — |

TABLE 1-continued

| | | | | | |
|---|---|---|---|---|---|
| SrO | — | — | — | — | — |
| ZnO | 8.7 | 8.6 | — | — | 8.3 |
| Al$_2$O$_3$ | 2.7 | 2.7 | 2.7 | 2.7 | 2.6 |
| Ga$_2$O$_3$ | — | — | — | — | — |
| La$_2$O$_3$ | — | — | — | — | — |
| Er$_2$O$_3$ | — | — | 0.1 | 0.1 | — |
| ZrO$_2$ | — | — | — | — | — |
| SnO$_2$ | — | — | — | — | — |
| CeO$_2$ | — | — | 0.8 | 1.5 | — |
| GeO$_2$ | — | — | — | — | 8.9 |
| MnO$_2$ | — | — | — | — | — |
| V$_2$O$_5$ | — | — | 0.1 | 0.1 | — |
| Ta$_2$O$_5$ | — | — | — | — | — |
| P$_2$O$_5$ | 6.3 | 5.0 | 3.8 | 3.7 | 4.2 |
| F$^-$ | — | — | — | — | — |
| Tb$_4$O$_7$ | — | — | 0.3 | 0.4 | — |
| T$_g$/° C. | 455 | 459 | 458 | 463 | |
| T$_s$/° C., t$_s$/min | 1500, 120 | 1500, 120 | 1500, 120 | 1500, 120 | 1400, 120 |
| T$_{Kb}$/° C., t$_{Kb}$/min | 500, 30 | 500, 30 | 500, 30 | 500, 30 | 500, 30 |
| T$_c$/° C., t$_c$/min | 840, 30 | 850, 30 | 800, 30 | 800, 30 | 820, 30 |
| T$_{press}$/° C., t$_{press}$/° C. | | | | | |
| Main crystal phase (wt.-%) | Li$_2$Si$_2$O$_5$, | Li$_2$Si$_2$O$_5$, | Li$_2$Si$_2$O$_5$, | Li$_2$Si$_2$O$_5$, (33.8) | Li$_2$Si$_2$O$_5$, |
| Further crystal phases (wt.-%) | Low quartz, Li$_3$PO$_4$ | Low quartz, Li$_3$PO$_4$ | Low quartz, Li$_3$PO$_4$, Cs$_{0.809}$AlSi$_5$O$_{12}$ | Low quartz, (15.6) Li$_3$PO$_4$, (5.8) Cs$_{0.809}$AlSi$_5$O$_{12}$ (10.0) | Low quartz, Li$_3$PO$_4$ |
| σ$_{Biax}$/MPa | 458 | 485 | 516 | 368 | |
| CR value | 90.90 | 86.57 | 73.4 | 73.54 | |
| L* | 95.87 | 95.52 | 90.36 | 82.05 | |
| a* | −0.24 | −0.24 | 0.32 | 4.63 | |
| b* | 0.84 | 0.66 | 11.49 | 26.02 | |
| CTE/10$^{-6}$K$^{-1}$ (100-500° C.) | | | | | |

The invention claimed is:

1. Lithium silicate-low quartz glass ceramic, which comprises 1.0 to 7.0 wt.-% Al$_2$O$_3$ and comprises lithium silicate as the main crystal phase and low quartz as further crystal phase.

2. Glass ceramic according to claim 1, which comprises 59.0 to 79.0 wt.-% SiO$_2$.

3. Glass ceramic according to claim 1, which comprises 8.0 to 15.0 wt.-% Li$_2$O.

4. Glass ceramic according to claim 1, which comprises 0 to 9.0 wt.-% P$_2$O$_5$.

5. Glass ceramic according to claim 1, which comprises 1.0 to 8.0 wt.-% oxide of monovalent elements Me$^I_2$O selected from the group of K$_2$O, Na$_2$O, Rb$_2$O, Cs$_2$O and mixtures thereof.

6. Glass ceramic according to claim 1, which comprises 0 to 5.0 wt.-% K$_2$O.

7. Glass ceramic according to claim 1, which comprises 1.0 to 9.0 wt.-% oxide of divalent elements Me$^{II}$O selected from the group of CaO, MgO, SrO, ZnO and mixtures thereof.

8. Glass ceramic according to claim 1, which comprises 1.0 to 6.0 wt.-% MgO.

9. Glass ceramic according to claim 1, which comprises 1.0 to 8.0 wt.-% oxide of trivalent elements Me$^{III}_2$O$_3$ selected from the group of Al$_2$O$_3$, B$_2$O$_3$, Y$_2$O$_3$, La$_2$O$_3$, Ga$_2$O$_3$, In$_2$O$_3$ and mixtures thereof.

10. Glass ceramic according to claim 1, which comprises 1.0 to 6.0 wt.-% Al$_2$O$_3$.

11. Glass ceramic according to claim 1, which comprises at least one of the following components in the amounts specified:

| Component | wt.-% |
|---|---|
| SiO$_2$ | 59.0 to 79.0 |
| Li$_2$O | 8.0 to 15.0 |
| P$_2$O$_5$ | 0 to 9.0 |
| Me$^I_2$O | 1.0 to 8.0 |
| Me$^{II}$O | 1.0 to 9.0 |
| Me$^{III}_2$O$_3$ | 0 to 8.0 |
| Me$^{IV}$O$_2$ | 0 to 10.0 |
| Ms$^V_2$O$_5$ | 0 to 8.0 |
| Me$^{VI}$O$_3$ | 0 to 5.0 |
| fluorine | 0 to 1.0, | wherein

Me$^I_2$O is selected from the group of K$_2$O, Na$_2$O, Rb$_2$O, Cs$_2$O and mixtures thereof, Me$^{II}$O is selected from the group of CaO, MgO, SrO, ZnO and mixtures thereof, Me$^{III}_2$O$_3$ is selected from the group of Al$_2$O$_3$, B$_2$O$_3$, Y$_2$O$_3$, La$_2$O$_3$, Ga$_2$O$_3$, In$_2$O$_3$ and mixtures thereof, Me$^{IV}$O$_2$ is selected from the group of ZrO$_2$, TiO$_2$, SnO$_2$, CeO$_2$, GeO$_2$ and mixtures thereof, Me$^V_2$O$_5$ is selected from the group of V$_2$O$_5$, Ta$_2$O$_5$, Nb$_2$O$_5$ and mixtures thereof, and Me$^{VI}$O$_3$ is selected from the group of WO$_3$, MoO$_3$ and mixtures thereof.

12. Glass ceramic according to claim 1, which comprises at least one of the following components in the amounts specified:

| Component | wt.-% |
|---|---|
| SiO$_2$ | 59.0 to 79.0 |
| Li$_2$O | 8.0 to 15.0 |
| P$_2$O$_5$ | 0 to 9.0 |

-continued

| Component | wt.-% |
|---|---|
| K$_2$O | 0 to 5.0 |
| Na$_2$O | 0 to 2.0 |
| Rb$_2$O | 0 to 8.0 |
| Cs$_2$O | 0 to 7.0 |
| CaO | 0 to 3.0 |
| MgO | 0 to 6.0 |
| SrO | 0 to 4.0 |
| ZnO | 0 to 9.0 |
| Al$_2$O$_3$ | 1.0 to 6.0 |
| B$_2$O$_3$ | 0 to 4.0 |
| Y$_2$O$_3$ | 0 to 5.0 |
| La$_2$O$_3$ | 0 to 5.0 |
| Ga$_2$O$_3$ | 0 to 3.0 |
| In$_2$O$_3$ | 0 to 5.0 |
| ZrO$_2$ | 0 to 3.0 |
| TiO$_2$ | 0 to 4.0 |
| SnO$_2$ | 0 to 3.0 |
| GeO$_2$ | 0 to 9.0 |
| CeO$_2$ | 0 to 4.0 |
| V$_2$O$_5$ | 0 to 2.0 |
| Ta$_2$O$_5$ | 0 to 5.0 |
| Nb$_2$O$_5$ | 0 to 5.0 |
| WO$_3$ | 0 to 3.0 |
| MoO$_3$ | 0 to 3.0 |
| fluorine | 0 to 1.0. |

13. Glass ceramic according to claim 1, which comprises SiO$_2$ and Li$_2$O in a molar ratio in the range of from 2.2 to 4.1.

14. Glass ceramic according to claim 1, which comprises lithium disilicate or lithium metasilicate as the main crystal phase.

15. Glass ceramic according to claim 1, which has at least 20 wt.-% lithium disilicate crystals.

16. Glass ceramic according to claim 1, which has 0.2 to 28 wt.-% low quartz crystals.

17. Glass ceramic according to claim 1, wherein the glass ceramic is present in the form of a powder, a granulate, a blank or a dental restoration.

18. Glass ceramic according to claim 1, wherein the main crystal phase is the crystal phase which has the highest proportion by mass of all the crystal phases present in the glass ceramic.

19. Process for the preparation of the glass ceramic according to claim 1, in which a starting glass is subjected to at least one heat treatment in the range of 700 to 900° C.

20. Process according to claim 19, in which
  (a) the starting glass is subjected to a heat treatment at a temperature of 400 to 600° C. in order to form a starting glass with nuclei for the crystallization of lithium metasilicate, lithium disilicate and/or low quartz, and
  (b) the starting glass with nuclei is subjected to a heat treatment at a temperature of 700 to 900° C. in order to form the lithium silicate-low quartz glass ceramic.

21. Process of using the glass ceramic according to claim 1 as dental material, for coating dental restorations or for the preparation of dental restorations.

22. Process for the preparation of a dental restoration comprising a bridge, inlay, onlay, veneer, abutment, partial crown, crown or facet, in which the glass ceramic according to claim 1 is given the shape of the desired dental restoration by pressing or machining.

23. Glass ceramic comprising lithium silicate as the main crystal phase and low quartz as further crystal phase, which is present in the form of a dental restoration, wherein the dental restoration comprises a bridge, inlay, onlay, veneer, abutment, partial crown, crown or facet.

* * * * *